United States Patent
Minkoff (10) Patent No.: US 9,504,429 B1
(45) Date of Patent: Nov. 29, 2016

(54) APPARATUS FOR CONTROLLING THE OPERATION OF AN MRI SYSTEM

(71) Applicant: Fonar Corporation, Melville, NY (US)

(72) Inventor: Lawrence A. Minkoff, Lattingtown, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 13/926,275

(22) Filed: Jun. 25, 2013

Related U.S. Application Data (60) Provisional application No. 61/665,547, filed on Jun. 28, 2012.

(51) Int. Cl.
| | |
|---|---|
| *A61B 5/055* | (2006.01) |
| *A61B 5/00* | (2006.01) |
| *G01R 33/567* | (2006.01) |
| *G01R 33/36* | (2006.01) |

(52) U.S. Cl.
CPC ............ *A61B 5/7285* (2013.01); *A61B 5/0006* (2013.01); *A61B 5/055* (2013.01); *G01R 33/3692* (2013.01); *G01R 33/5673* (2013.01)

(58) Field of Classification Search
CPC .. A61B 5/055; A61B 5/0006; A61B 5/7285; G01R 33/3692; G01R 33/5616; G01R 33/56375; G01R 33/56383; G01R 33/5673; H04L 29/12943; H04L 61/6072; H04W 76/021; H04W 76/023; H04W 84/18
See application file for complete search history.

(56) References Cited

U.S. PATENT DOCUMENTS

| | | | |
|---|---|---|---|
| 4,903,704 A * | 2/1990 | Van Eggermond et al. .. | 600/413 |
| 6,032,069 A * | 2/2000 | Elgavish et al. .............. | 600/413 |
| 6,052,614 A * | 4/2000 | Morris et al. ................. | 600/509 |
| 7,590,439 B2 * | 9/2009 | Raridan ............ | A61B 5/14552 600/344 |
| 8,433,382 B2 * | 4/2013 | Li ........................ | A61B 5/0261 600/310 |
| 2002/0049389 A1 * | 4/2002 | Abreu ........................... | 600/558 |
| 2006/0226841 A1 * | 10/2006 | Boskamp et al. ............. | 324/322 |
| 2006/0241392 A1 * | 10/2006 | Feinstein et al. ............. | 600/422 |
| 2010/0046443 A1 * | 2/2010 | Jia et al. ........................ | 370/329 |
| 2010/0087729 A1 * | 4/2010 | Takizawa et al. ............. | 600/413 |
| 2010/0113902 A1 * | 5/2010 | Hete et al. ..................... | 600/323 |
| 2011/0074409 A1 * | 3/2011 | Stoughton et al. ........... | 324/307 |
| 2014/0171783 A1 * | 6/2014 | Schmidt et al. .............. | 600/413 |

FOREIGN PATENT DOCUMENTS

WO    WO 0064335 A1 * 11/2000

* cited by examiner

*Primary Examiner* — Ruth S Smith
(74) *Attorney, Agent, or Firm* — Lerner, David, Littenberg, Krumholz & Mentlik, LLP (57) ABSTRACT

An MRI system is provided that includes a physiological sensor used for gating the MRI system and an MRI control terminal wirelessly connected to the sensor. The physiological sensor is used to monitor a physiological parameter of a user, such as pressure pulse, and communicate data regarding the monitored physiological parameter to the MRI control terminal. The MRI control terminal processes the data received from the physiological sensor and determines whether a triggering condition on the data is met. When it is determined that the triggering condition is met, the MRI control terminal initiates the acquisition of a data set. The acquisition of the data set involves initiating a pre-programmed pulse sequence and acquiring RF signals emitted from the patient's tissue as a result of the execution of the pre-programmed pulse sequence.

15 Claims, 9 Drawing Sheets

| MRI Control Terminal Wireless Sensor Connection Menu | | |
|---|---|---|
| *Sensor ID* | *Sensor Type* | *Signal Strength* |
| Sensor_1 | photoplethysmograph | 87% |
| Sensor_2 | ECG sensor | 52% |

CANCEL    CONNECT

APPARATUS FOR CONTROLLING THE OPERATION OF AN MRI SYSTEM

CROSS-REFERENCE TO RELATED APPLICATIONS

The present application claims the benefit of the filing date of U.S. Provisional Patent Application No. 61/665,547 filed Jun. 28, 2012, the disclosure of which is hereby incorporated in its entirety herein by reference.

BACKGROUND

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automatic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

As discussed above, MRI images are taken by acquiring multiple sets of MRI data and compounding those sets to produce a single MRI image. For many years it has been desirable to collect each data set when a predetermined physiological event occurs. The event may be a respiratory event, a muscle movement, a cardiac motion, or any other physiological event. In that regard, in MRI applications, it is often necessary to have the ability to accurately gate the MRI system so the data may be collected when the physiological event occurs.

In some instances, of particular interest in MRI applications is the ability to time the acquisition of data to one point during the cardiac cycle. The most common point used is ventricular contraction, as visualized on the electrocardiogram (ECG) as the QRS wave. The contraction also produces a pressure pulse that is transmitted throughout the whole arterial system of a patient. Using the ECG as a gating technique has been the standard used for years. Nevertheless, there are several disadvantages inherent in using ECG in MRI gating. First, there are fast switching magnetic gradients that induce currents in wires that connect to ECG sensors. Similarly there are induced currents in the skin of the subject that also interfere with the acquisition of the ECG. And finally, there are safety concerns about wires that are in contact with the patient as currents might be induced in those wires by the MRI systems.

SUMMARY

In one aspect, an MRI system is provided that includes a physiological sensor used for gating the MRI system and an MRI control terminal wirelessly connected to the sensor. The physiological sensor is used to monitor a physiological parameter of a user, such as pressure pulse, and communicate data regarding the monitored physiological parameter to the MRI control terminal. The MRI control terminal processes the data received from the physiological sensor and determines whether triggering condition on the data is met. When it is determined that the triggering condition is met, the MRI control terminal initiates the acquisition of a data set. The acquisition of the data set involves initiating a pre-programmed pulse sequence and acquiring RF signals emitted from the patient's tissue as a result of the execution of the pre-programmed pulse sequence.

DETAILED DESCRIPTION

Figure 1:
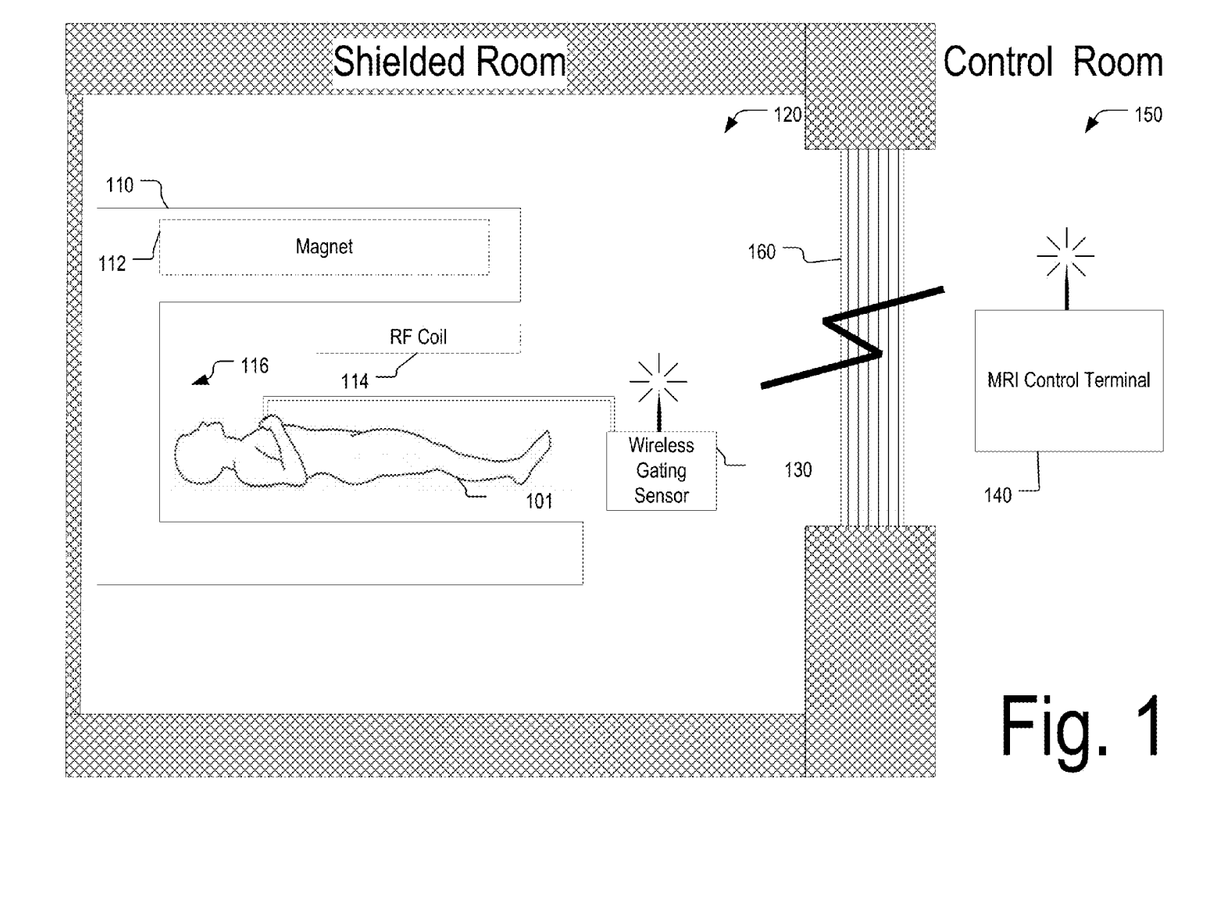
FIG. 1 depicts a schematic diagram of an MRI system in accordance with aspects of the disclosure.

FIG. 1 depicts a schematic diagram of an MRI system. The system comprises a magnet subsystem 110 that includes a magnet 112 for generating a polarizing static magnetic field surrounding a patient imaging volume 116. The magnet subsystem 110 further includes gradient coils (not shown) for creating gradients used to determine the spatial localization of the magnetic resonance signals from the patient. The excitations result in RF responses being received from the patients' 101 tissue via a coil 114, which, in turn, are used to create MRI images of the patient 101. The magnet subsystem 110 is located in a shielded room 120 in order to minimize RF interference on the MR imaging process. As noted above, multiple excitations of the patient's tissue may be necessary to acquire a single MRI image.

The physiological sensor 130 is a sensor that monitors a physiological parameter of the patient 101 for use in gating the MRI system. The physiological sensor 130 may be a photoplethysmograph, oxymeter, an EKG sensor, or any sensor that detects heartbeat, respiration, blood pulse, or another physiological parameter suitable for use in gating MRI systems. In this example, the physiological sensor 130 is a photoplethysmograph that monitors the pressure pulse of the patient 101.

The MRI control terminal 140 includes hardware and software for controlling the timing of data acquisition by the magnet subsystem 110. The MRI control terminal 140 is situated in a control room 150 that is separated from the shielded room 120 by a window 160. The MRI control terminal is operatively connected to the MRI system. In addition, the MRI control terminal is connected to the physiological sensor 130 via a wireless connection that operates at a frequency high enough to pass through the window 160. The connection may be a Wi-Fi connection (e.g., 802.11 operating at 2.5 GHz) or another type of connection. Using a wireless connection to connect the physiological sensor 130 to the MRI control terminal 140 avoids some of the problems that are inherent in using fiber optic and copper wires, such as current induction in the wires and disturbing the shielding of the shielded room 120 in order the run the wires.

In operation, the MRI control terminal 140 may receive data from the physiological sensor 130 and compile the data to produce a waveform of the pressure pulse of the patient 101. The waveform may be presented on a display screen of the MRI terminal 140 for viewing by an operator. The MRI control terminal 140 may further monitor the waveform edge and determine whether a triggering condition on the waveform is satisfied. The triggering condition may involve the waveform reaching predetermined amplitude, or assuming another waveform characteristic related to the waveform's amplitude, shape, frequency, or periodicity. When it is determined that the triggering condition is met, the MRI control terminal 140 may transmit a triggering signal to the MRI system. Upon receiving the triggering signal, the MRI system will cause the magnet subsystem 110 to execute an MRI pulse sequence and acquire a new set of MRI data using the coil 114.

In this example, the MRI control terminal 140 includes a user interface that gives the operator complete control over when triggering signals are produced. In one aspect, the MRI control terminal may provide the operator with a user interface that enables the operator to manually control the base line value of the waveform and set the amount of gain of the signal. In another aspect, the user interface of the MRI control terminal 140 may enable the operator to manually set the triggering condition. For example, the user interface may allow the operator to set the triggering condition either on a rising or falling part of a pressure pulse. As another example, the user interface may enable the operator to set the triggering condition on a specific amplitude value (e.g., configure the MRI system to acquire a data set when a pulse reaches specified amplitude). In yet another aspect, the user interface may allow the operator to specify a minimum delay between the transmissions of subsequent triggering signals. If the triggering condition is satisfied before the minimum delay has expired, the MRI control terminal 140 may refrain from transmitting another triggering signal. Specifying a minimum delay may prevent a second unwanted trigger on a noisy signal. (e.g., once a trigger is issued a second trigger cannot be generated for example in the next 0.3 seconds.)

In some instances, the user interface of the MRI control terminal 140 may allow the operator to choose between manual mode and automatic mode. When in automatic mode, the MRI control terminal 140 may set the gain and/or base value automatically. Applying gain to the physiological signal that is used to gate the MRI system enables small signals to be amplified by a value greater than one while strong signals are amplified by values less than one. In practice, the peak value of the pressure pulse may vary throughout a data acquisition time frame. Thus, when in automatic mode, the MRI control terminal 140 will automatically recalculate the gain value periodically (e.g., every ten seconds).

Figure 2:
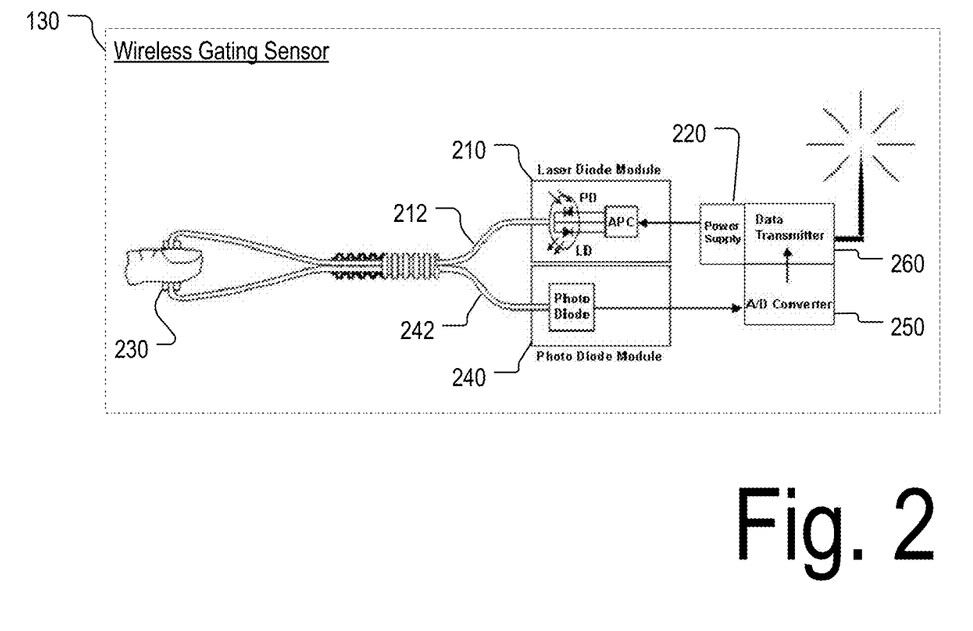
FIG. 2 depicts a schematic diagram of a physiological sensor used in gating the MRI system of FIG. 1.

FIG. 2 depicts a schematic diagram of the physiological sensor 130. As illustrated, the physiological sensor 130 is a photoplethysmograph including a diode 210, a power supply 220, photodiode 240, an A/D converter 250, and a wireless transceiver 260. The diode 210 is a Laser diode in the visible red part of the visible light spectrum (650 nm). The diode 210 is powered using the power supply 220. The diode 210 is connected via a plastic fiber-optic cable 212 to a probe 230 that is attached to the finger of the patient 101. Similarly, the photo diode 240 is also coupled via a plastic fiber-optic cable 242 to the probe 230. In operation, the diode 210 emits light across the fingertip of the patient 101 and the photodiode 240 detects light passing through the fingertip of the patient 101 and converts it into an electric signal. The electric signal is filtered and digitized using the A/D converter 250. The digitized signal is fed to the wireless transceiver 260 and transmitted to the MRI control terminal 140. Afterwards, the digitized signal is used by the MRI control terminal 140 to compile a pressure pulse wave for the patient 101. Deriving a pressure pulse wave from the sensor data is possible because the scattering of light passing through the finger tip of the patient depends, at least partially, on the amount of blood present in the finger. The amount of blood varies with the pulsating blood flow of the patient.

In some aspects, the wireless transceiver 260 may include a Wi-Fi transceiver, a Bluetooth transceiver, or any other type of transceiver. Furthermore, the sensor 130 may include a processor coupled to a memory (not shown). The memory may be configured to store an identifier, such as a unique sensor identifier, a manufacturer's ID, a model number, or an identifier of an MRI system associated with the physiological sensor 130. The processor may be arranged to transmit an indication of the identifier either periodically or in response to a request from the MRI control terminal 140. The processor, the memory, and the wireless transceiver 260 may be integrated into the same physical housing as other sensor components or they may have a separate housing.

Figure 3:
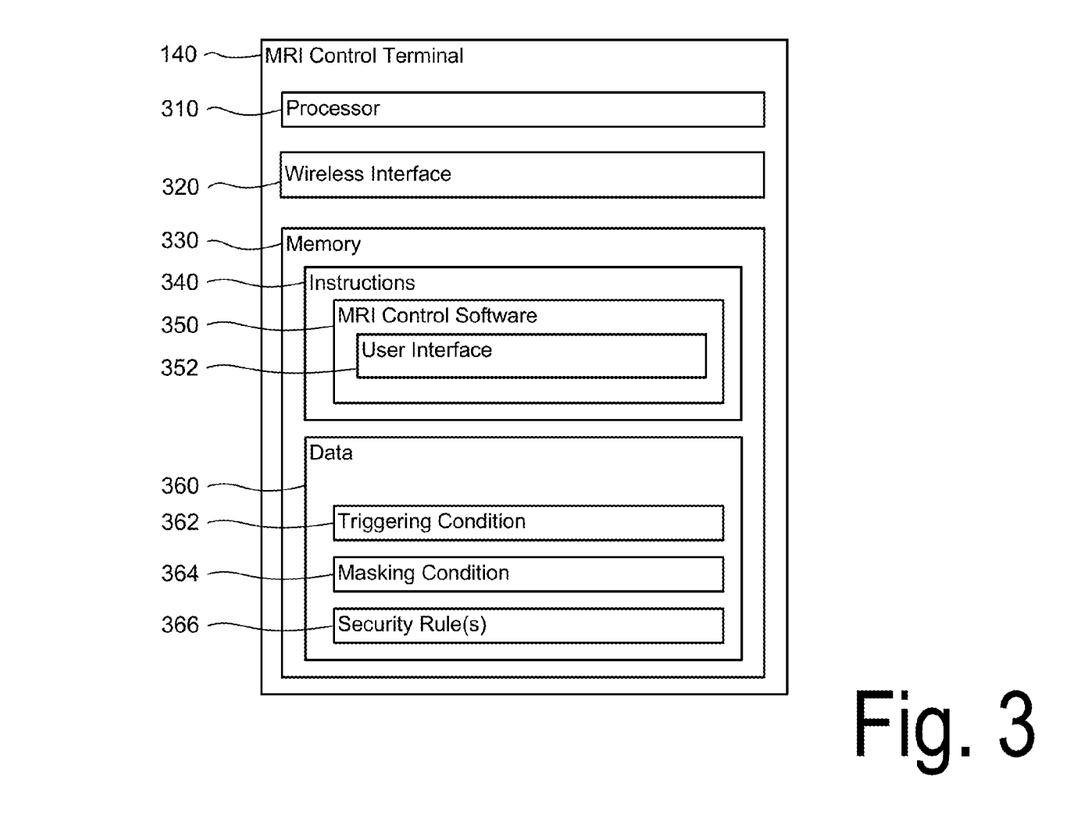
FIG. 3 depicts a schematic diagram of a MRI control terminal that is part of the MRI system of FIG. 1.

FIG. 3 depicts a schematic diagram of the MRI control terminal 140 in accordance with aspects of the disclosure. As shown, the MRI control terminal 140 includes a processor 310, a wireless interface 320, and a memory 330. Memory 330 stores information accessible by processor 310, including instructions 340 that may be executed by the processor 310. The memory also includes data 360 that may be retrieved, manipulated or stored by the processor. The memory may be of any type capable of storing information accessible by the processor, such as a hard-drive, memory card, ROM, RAM, DVD, CD-ROM, write-capable, and read-only memories. The processor 310 may be any well-known processor, such as commercially available processors. Alternatively, the processor may be a dedicated controller such as an ASIC. In some aspects, the processor 310 may be operable to receive data from the physiological sensor 130 via the wireless interface 320. The wireless interface 320 may be a Wi-Fi interface, a Bluetooth interface, or any other type of transceiver capable of communicating with the wireless transceiver 260 of the physiological sensor 130.

The instructions 340 may be any set of instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. The instructions 340 may include control software 350 for gating the MRI system. The software 350 includes user interface 352 for specifying a various parameters related to the gating of the MRI system. By way of example, the user interface may be used to specify a triggering condition, a base value for the physiological signal waveform, a masking condition (e.g., minimum delay), sensor security rules, or a gain. In some aspects, the user interface 352 may include a plurality of graphical user interface screens (GUIs), such as the GUI 500, depicted in FIG. 5, and the GUI 600, depicted in FIG. 6. These GUIs are discussed further below.

Data 360 may be retrieved, stored or modified by processor 310 in accordance with the instructions 340. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

As illustrated, the data 360 may store an indication of triggering condition 362, an indication of a masking condition 364, and an indication of a sensor security rule 366. The triggering condition 352, as noted above, may identify a characteristic of the physiological waveform that is derived from data transmitted by the physiological sensor 130. By way of example, the triggering condition may include one or more of:

T1: An indication of a slope of the waveform (e.g., generate a triggering signal on a rising edge; generate a triggering signal on a falling edge).

T2: An indication of an amplitude value of the gating signal wave (e.g., generate a triggering signal when the waveform of the patient's 101 pressure pulse reaches amplitude of 150).

T3: An indication of a waveform pattern (e.g., trigger a data acquisition when a predetermined pattern is observed in the waveform). The indication of the pattern may be based on at least one of order, duration, and magnitude of one or more local maxima (e.g., pulses in the waveform). An example of a pattern may be one that is characterized by a first local maximum that is both preceded and succeeded by local maxima that are at most 50% of the first local maxima. Another example of a pattern may be one characterized by a first waveform pulse that is at least 20% shorter in duration than the pulse immediately preceding the first waveform pulse.

The masking condition 354 may be any condition that, if satisfied, leads to the MRI terminal ignoring the occurrence of a triggering event and refraining from transmitting a triggering signal to the magnet subsystem 110 when the triggering event occurs. For example, the masking condition may specify that at least 10 milliseconds must pass between the generations of successive triggering signals. As another example, the masking condition may specify that if the slope of rising waveform edge is too steep, that edge should be ignored. As yet another example, the masking condition may specify that when a predetermined waveform pattern occurs, no triggering signals should be transmitted by the MRI control terminal 120. In any event, the masking condition 364 may prevent unwanted triggering signals from being transmitted due to noise being present in the signal from the physiological sensor 130.

The security rule(s) may include one or more indications of characteristics that should be possessed by a wireless sensor, such as the physiological sensor 130, before a connection can be established between that sensor and the MRI control terminal 140. The security rule(s) may be specified, via an input device such as keyboard, by an operator of the MRI system, or they may be preprogrammed into the MRI control terminal by the system's manufacturer. Examples of security rules include:

R1: Establish a connection with a sensor only when the strength of signal from that sensor exceeds a predetermined threshold. A rationale for having this rule may be that if the signal strength is low, the connection between the wireless physiological sensor 130 and the MRI control terminal 140 may fall apart before an MRI image has been acquired.

R2: Establish a connection with a sensor having an identifier only if an identifier associated with the sensor is found on a list of identifiers of sensors that are permitted to connect to the MRI control terminal 140. The identifier may be one that is unique to the sensor, a manufacturer's ID, a model number, or another identifier. The list of identifiers may be stored in the memory 330 or elsewhere. A rationale for having this rule may be to prevent using wireless physiological sensors that have not been tested for compliance with the MRI control terminal 140.

R3: Establish a connection with a sensor only if the sensor identifies itself as being associated with the MRI system. In some instances, sensors may be programmed to store in their memory an identifier of an MRI system they are associated with. Such sensors may be arranged to transmit the identifier to the MRI managing terminal upon request, or otherwise. A rationale for having this rule may be to prevent the MRI terminal 140 from gating the operation of the MRI system based on signals from the wrong sensor (e.g., a sensor in another room).

Although FIG. 3 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Figure 4:
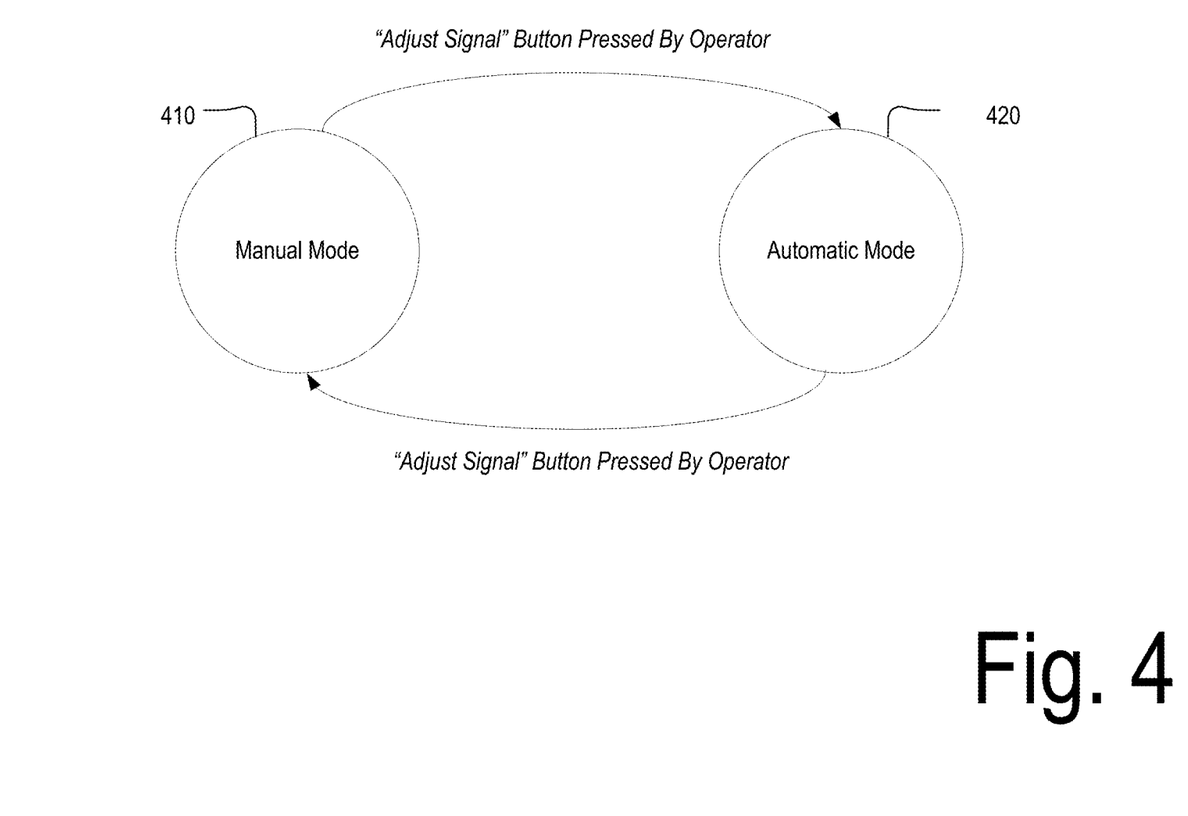
FIG. 4 depicts a state machine chart of MRI control software that is executed by the MRI control terminal of FIG. 3.

FIG. 4 depicts a state machine diagram for the MRI control terminal 140. According to this example, the MRI control terminal 140 can be in either a manual mode state 410 or automatic mode state 420. When in the manual mode state 410, the gain on the signal from the gate sensor is set manually by the operator. Furthermore, a graphical user interface (GUI) 500 (FIG. 5) is presented to the operator on a display screen of the MRI control terminal 140. As illustrated, the GUI 500 includes a pane 510 for displaying a graph of waveform 512 representing a physiological parameter of the patient 101 (e.g., pressure pulse). The waveform is based on the signal received by the MRI control terminal 140 from the physiological sensor 130.

Figure 5:
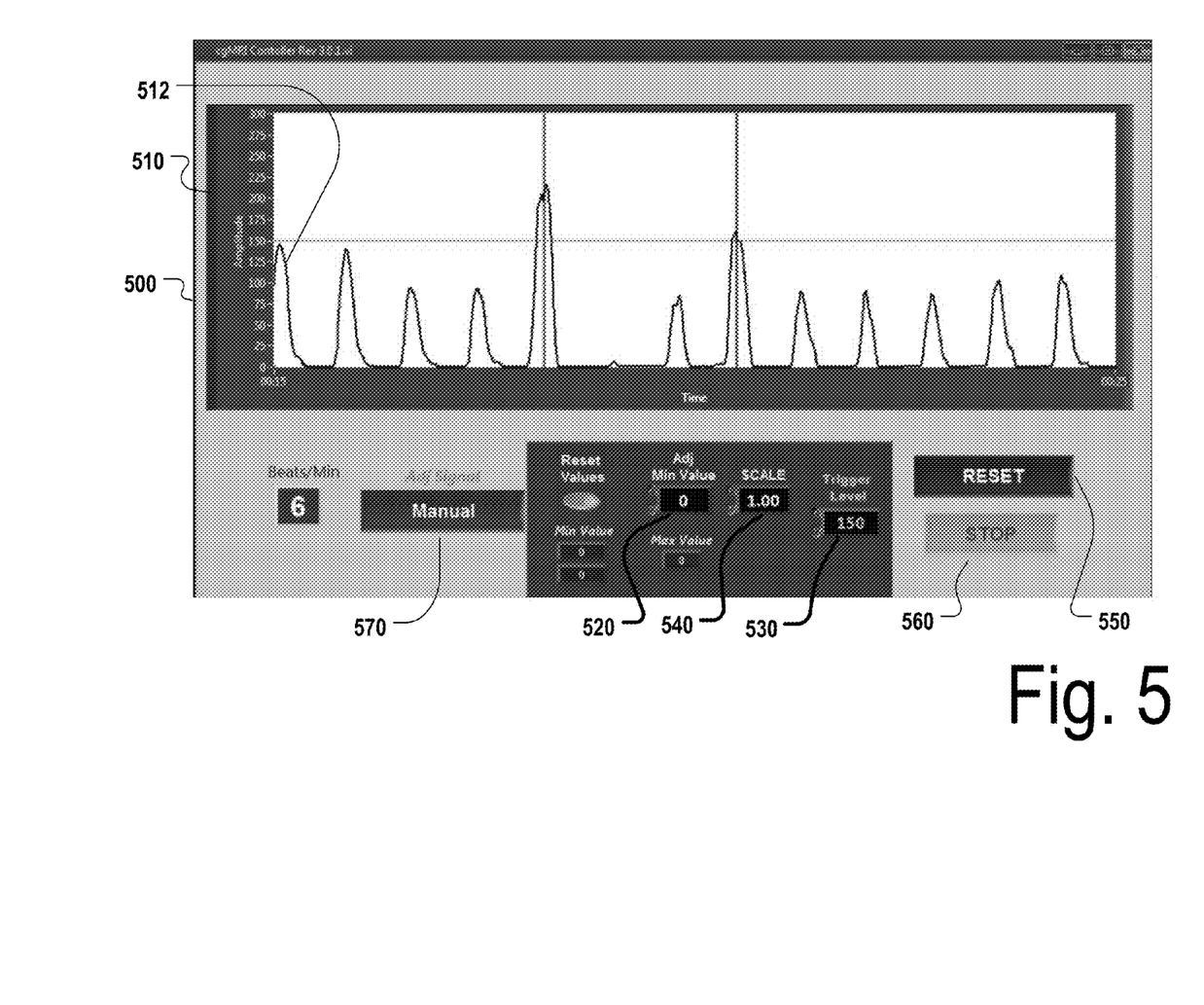
FIG. 5 depicts a graphical user interface (GUI) of the MRI control application of FIG. 4.

In one aspect, as discussed above, the GUI 500 may include one or more input components for specifying various parameters related to the gating of the MRI system. In this example, the GUI 500 includes an input component 520 for specifying a base value for the waveform 512, an input component 530 for specifying the triggering condition (e.g., a waveform amplitude the reaching of which would trigger the acquisition of a data set by the MRI system), and an input component 540 for specifying gain. Furthermore, the GUI 500 may include a "Reset" button 550 for returning various gating parameters (e.g., base value, triggering condition, gain) to predetermined default values, a "Stop" button 560 for stopping the acquisition of data by the MRI system, and an "Adjust Signal" button 570. When the "Adjust Signal" button 570 is pressed the state of the MRI control terminal may be toggled from "Automatic" to "Manual," and vice versa. Furthermore, in this example, the "Adjust Signal" button 570 is outfitted with a label that indicates what state the MRI control terminal 140 is in.

Figure 6:
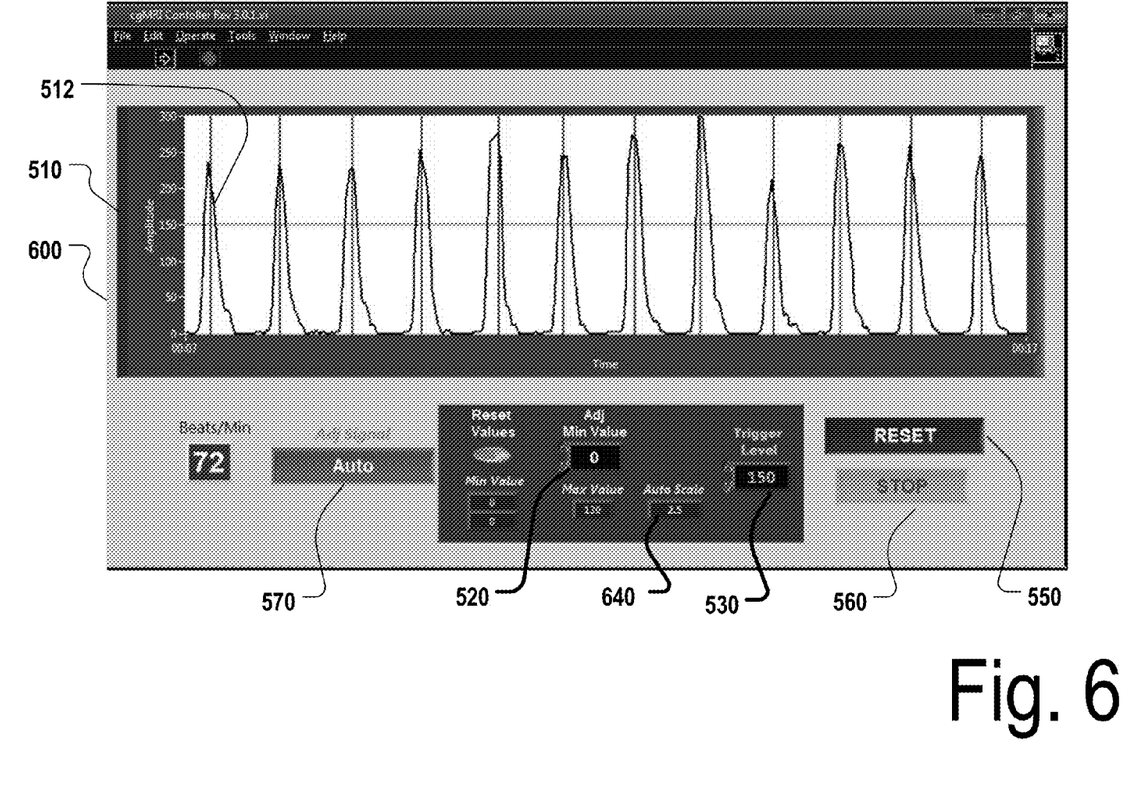
FIG. 6 is a graph a GUI of the MRI control application of FIG. 4.

When the MRI control terminal 140 is in the automatic mode state 420, the gain of the signal from the gating sensor is determined automatically by MRI control terminal 140. Furthermore, in the state 420, the GUI 600 is presented to the operator on the display screen of the MRI control terminal 140. As illustrated, the GUI 600 is almost identical to the GUI 500 except for that it lacks the input component 540 for specifying gain. Instead, the GUI 600 is outfitted with an indicator 640 (e.g., a text field) that indicates the gain (e.g. scale value) that has been automatically calculated by the MRI control terminal 140 and is currently in use . . . . . Although in this example the input components for specifying the triggering level (e.g., triggering condition), signal base value, and gain are text fields, in other examples they may be any other type of input component (e.g., radio buttons, list menus, drop-down menus, sliders, or knobs).

Figure 7:
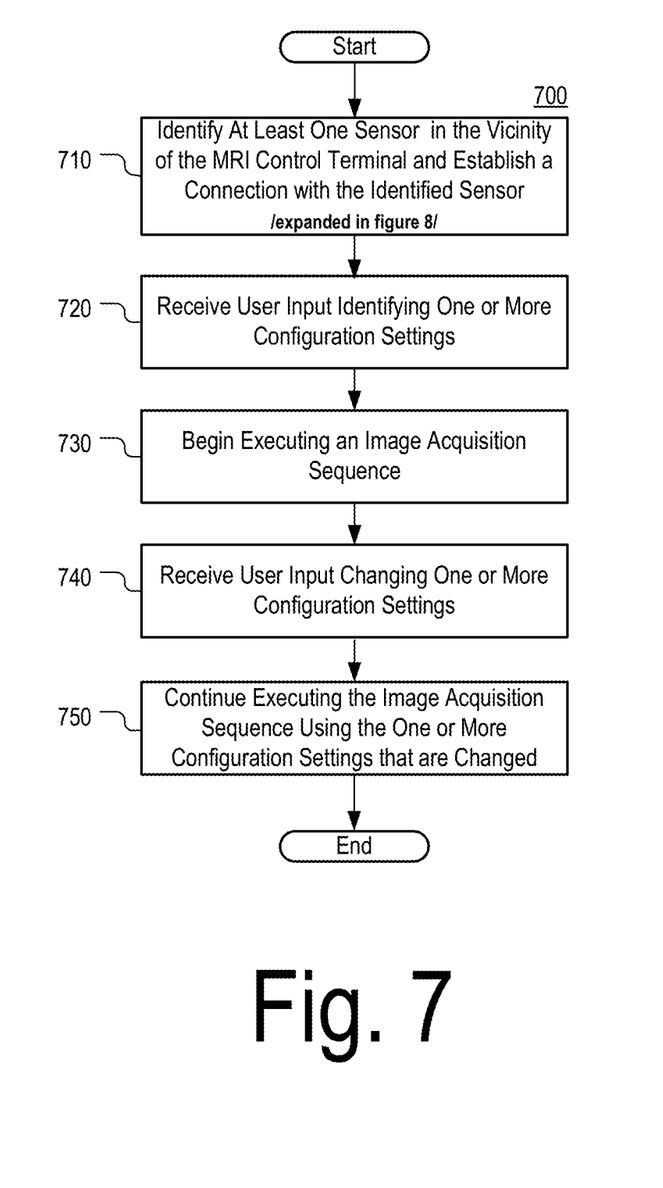
FIG. 7 depicts a flowchart of a process associated with the operation of the MRI control system of FIG. 1.

FIG. 7 depicts a flowchart of a process 700 associated with the operation of the MRI control terminal 140. At task 710, the MRI control terminal 140 identifies one or more wireless sensors and establishes a connection with one of the identified sensors. In this example, a connection with the physiological sensor 130 is established.

At task 720, the MRI control terminal 140 receives user input specifying a first triggering condition for use in acquiring data. More particularly, the user input may be any indication of a property of the physiological signal waveform (e.g., pressure pulse waveform), such as amplitude, slope (e.g., trigger on rising edge, trigger on falling edge), shape, or any other characteristic. The user input may be received from a text field, such as the field 530, or any other input component (e.g., radio button, drop down menu, list, or checkbox).

At task 730, the MRI control terminal 140 begins executing an image acquisition sequence. Executing the image acquisition sequence involves acquiring a plurality of MRI data sets for use in generating a single MRI image. The acquisition of each data set may be synchronized with the occurrence of a particular physiological event (e.g., ventricular contraction). This synchronization is accomplished by using a physiological signal, such as the signal supplied by the physiological sensor 130. Each of the acquired data sets will include information that is acquired by the MRI system as a result of the execution of an MRI pulse sequence.

In some aspects, while executing the image acquisition sequence, the MRI control terminal 140 may monitor the waveform of the signal received from the physiological sensor 130 and determine whether the triggering condition specified at task 720 is satisfied. Whenever the triggering condition is satisfied, a triggering signal is transmitted by the MRI control terminal 140 to the magnet subsystem 110. The triggering signal causes the magnet subsystem 110 to acquire a new data set and forward the acquired data set to the MRI control terminal 140.

At task 740, the MRI control terminal 140 receives user input identifying a second triggering condition that is different from the first triggering condition. The second triggering condition is provided as a substitute for the first triggering condition. The second triggering condition, is received before the image acquisition sequence initiated at task 730 is completed. In this example, the first triggering condition requires the MRI control terminal 140 to transmit a triggering signal to magnet subsystem 110 whenever the pressure pulse waveform measured by the sensor 130 reaches amplitude of 150, whereas the second triggering condition requires the MRI control terminal 140 to transmit a triggering signal whenever the pressure pulse waveform reaches amplitude 130. At task 750, the MRI control terminal 140 completes the image acquisition sequence using the second triggering condition that is specified at task 740. In that regard, a portion of the data sets acquired as a result of the execution of the image acquisition sequence are obtained using the first triggering condition while another portion of the data sets is obtained by using the second triggering condition. Thus, data sets from both portions may be used in the generation of a single MRI image (e.g., by the MRI control terminal 140).

For example, an operator may begin acquiring an MRI image of a patient using amplitude value of 150 as a triggering condition. However, halfway through the execution of the image acquisition sequence, the blood pressure of the patient may fall for some unexplained reason thereby causing the pressure pulse waveform measured by the sensor 130 to remain consistently under the amplitude value that is set to trigger data acquisition by the MRI system. In such instances, the operator may notice the blood pressure drop by viewing a graph of the pressure pulse wave form. Furthermore, in response, the operator may lower the triggering condition by using the user interface 352. Put another way, in one aspect, the MRI terminal 140 enables the operator of the MRI system to react to changing circumstances during the acquisition of an MRI image by changing the condition that triggers data acquisition by the MRI system. Although in the above example, the triggering condition used for gating the MRI system is changed, in other examples, the operator may change or enter a new masking condition midway through the execution of an image acquisition sequence.

Figure 8:
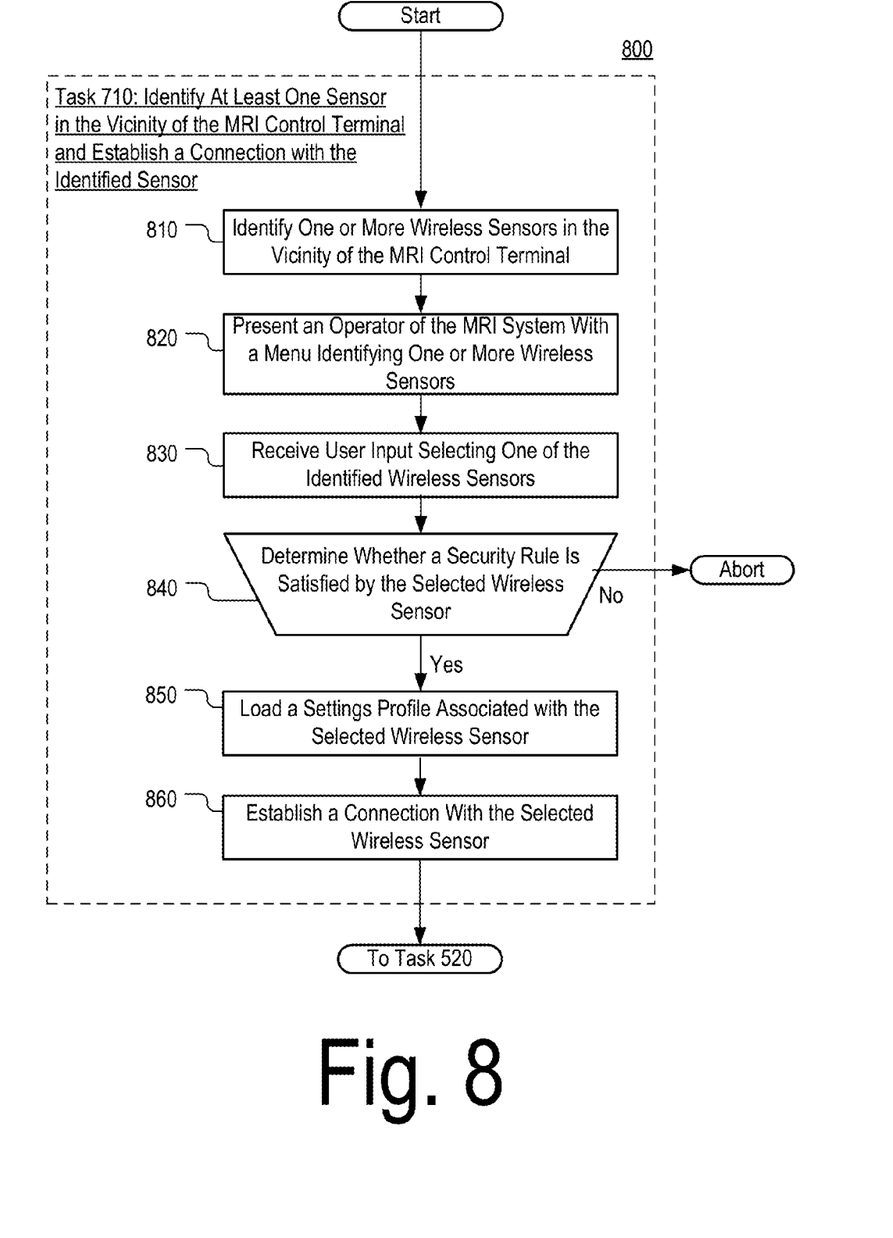
FIG. 8 depicts a flowchart of a sub-process associated with the process of FIG. 7.

FIG. 8 depicts a flowchart of a process 800 associated with identifying and connecting to wireless physiological sensor as specified by task 710 of FIG. 7. At task 810, the MRI control terminal 140 identifies one or more wireless physiological sensors in its vicinity. The wireless sensors may be identified based on a beacon signal, or other identifier signal, that is transmitted (or broadcast) by each one of the wireless sensors. The beacon signal (or identifier signal) may identify at least one of the following for each sensor:

B1: Type of sensor (e.g., pulse sensor, EKG sensor, oximeter, photoplethysmograph).

B2: Sensor manufacturer.

B3: Unique Identifier of a sensor (e.g., a number, or a string uniquely identifying the sensor, such as a MAC address).

B4: Unique identifier of an MRI system associated with the sensor (e.g., each sensor may be programmed to be associated with a given MRI system by storing in a memory of the sensor an identifier corresponding to the MRI system).

Figure 9:
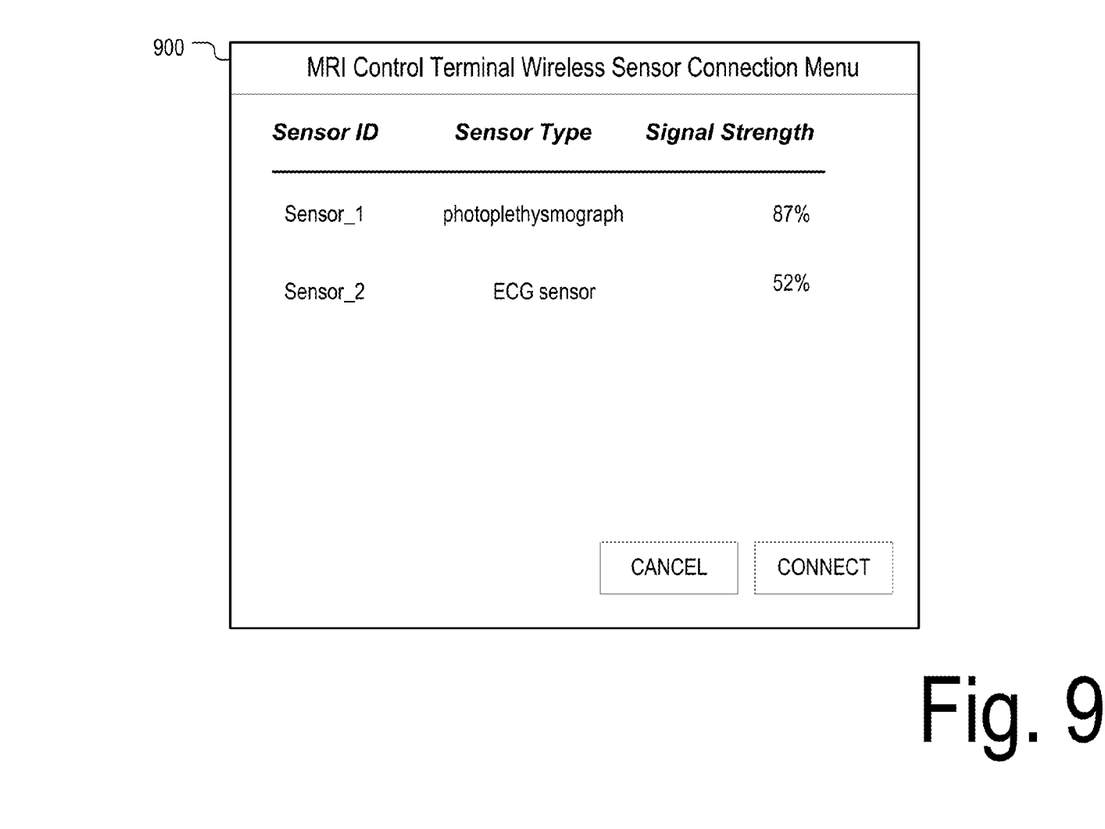
FIG. 9 depicts a schematic diagram of a menu for the selection of a wireless sensor.

At task 820, the operator of the MRI system is presented with a sensor selection menu, such as the menu 900 depicted in FIG. 9. As illustrated, the menu may list information regarding each of the sensors identified at task 810, such as a sensor ID, a sensor type, or strength of signal from the sensor. The information may be retrieved from beacon signals transmitted by each sensor or acquired as a result of a handshake executed after each sensor has been initially identified. At task 830, user input is received by the MRI control terminal 140 that identifies a user selection of a sensor identified in the selection menu. For example, the user input may involve highlighting one of the sensors listed in the menu 900 and subsequently clicking on the "Connected" button that is located in the bottom right corner of the menu.

At task 840, the MRI control terminal 140 determines whether one or more of the security rule(s) 366 are satisfied. If the security rule(s) are satisfied, the execution of the process 800 continues to task 850. Otherwise, if one or more rules are not satisfied, the execution of the process 800 is aborted.

At task 850, a settings profile associated with the sensor selected at task 820 is loaded. The settings profile may be a file or a data structure identifying one or more MRI parameters associated with the sensor. By way of example, the MRI parameters may include an indication of a triggering condition, an indication of a desired gain, or an indication of a masking condition. The settings profile may be identified by searching the memory 330, or the memory of a remote computer, for a file that is associated, via a look-up table or another similar structure, to an identifier of the sensor. By way of example, the identifier may be unique sensor ID, a manufacturer's ID, or a model number. Loading the profile may involve retrieving the profile and configuring the software 350 to use the one or more settings identified in the profile when gating the MRI system.

At task 860, a connection with the wireless sensor selected at task 830 is established. Only after the connection is established, may the MRI control terminal 140 begin acquiring data transmitted by the selected wireless sensors for use in gating the MRI system.

FIGS. 7-8 are provided as examples. At least some of the tasks associated with FIGS. 7-8 may be performed in a different order than represented, performed concurrently or altogether omitted. Furthermore, it should be noted that in some instances only the probe 230 of the physiological sensor 130 may be located inside the patient imaging volume 116 of the magnet subsystem 110 while at least some of the other components of the physiological sensor 130 are kept outside of the magnet subsystem 110. The fiber-optic cables 212 and 242 may extend between the probe and the other components, thereby permitting the other components to be located outside of the magnet subsystem 110. Moreover, although in the above examples the MRI system is a recumbent MRI system, in other examples it may be an upright MRI system, or any other type of MRI system. As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.," "including" and the like) should not be interpreted as limiting the claimed subject matter to the specific examples; rather, the examples are intended to illustrate only some of many possible aspects.

In summary, and as an example only, in one aspect a sensor for monitoring a physiological phenomenon in a patient is provided. The sensor comprises a wireless transceiver, a memory, and processor. The memory of the sensor is configured to store an identifier associated with a magnetic resonance image (MRI) system that identifies uniquely the MRI system from among a plurality of MRI systems. The processor is coupled to the wireless transceiver and is configured to transmit, using the wireless transceiver, an indication of the identifier associated with the MRI system. The sensor may include an oximeter, photopletismograph, ECG sensor, or any type of sensor capable of monitoring a physiological activity of a patient. The wireless transceiver operates at a base frequency capable of penetrating a window of a shielded room used for the conduct of MRI scans. The wireless transceiver is a Bluetooth transceiver, Wi-Fi transceiver, or wireless USB transceiver. The physiological phenomenon may be cardiac pulse, respiratory pulse, heart electrical activity.

As another example, a system is provided that includes a memory configured to store an indication of a first waveform characteristic and a processor coupled to the memory. The processor is configured to receive a signal indicating a physiological parameter of a patient, the signal having an associated waveform. The processor is further configured to execute an image acquisition sequence that includes acquiring a plurality of data sets, wherein each of the data sets is acquired by the MRI system when the waveform of the signal indicating a physiological parameter meets a predetermined triggering condition. The processor is further configured to receive, before the execution of the image acquisition sequence has been completed, a user input indicating a second waveform characteristic that is different from the first waveform characteristic. The plurality of data sets acquired during the first acquisition sequence includes a first proper subset and a second proper subset. The data sets in the first subset are acquired using the first waveform characteristic as the triggering condition. The data sets in the second subset are acquired using the second waveform characteristic as the triggering condition.

Using the first waveform characteristic as a triggering condition, when acquiring a data set, includes determining whether the signal indicating the physiological parameter of the patient possesses the first waveform characteristic. When it is determined that it does, the processor generates a triggering signal that causes a magnet subsystem of the MRI system to activate one or more magnetic gradients (or magnetic gradient coils) and collect RF data emitted by a subject's tissue as a result of nuclei in the tissue being excited by the magnet subsystem. The physiological parameter may be breathing pulse, heart pulse, heart electrical activity, or any other physiological parameter capable of being used in MRI gating.

The first waveform characteristic depends on at least one of frequency, slope, phase, and amplitude of the waveform of the physiological signal. In some aspects, the first indication may indicate a particular slope value, phase value or an amplitude value. The second waveform characteristic depends on at least one of frequency, slope, phase, and amplitude of the waveform of the physiological signal. In some aspects, the second indication may indicate a particular slope value, phase value or an amplitude value. In some aspects, both the first indication and the second indication may indicate different values for the same type of characteristic (e.g., different amplitude values). In other aspect, the first indication and the second indication may indicate values for different types of characteristics.

In yet another example, a device for gating an MRI system is provided. The device includes a wireless interface, a processor, and a display screen. The processor is configured to present on the display screen a menu identifying a plurality of wireless sensors that are present in the vicinity of the device. One or more of the wireless sensors may be sensors for measuring a physiological parameter of a subject that usable for gating the MRI system. The processor is further configured to receive user input selecting one of the devices, determine whether a security condition is met, and establish a connection. Furthermore, the processor may be further configured to load a profile associated with the selected wireless sensor. The profile may be a file or data structure indicating a triggering condition or a masking condition. After the profile is loaded, the processor begins using the triggering condition and/or masking condition when gating the MRI system. In another aspect, the processor may be further configured to present on the display screen a waveform associated with a signal received from a physiological sensor and receive user input indicating a triggering condition.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A magnetic resonance imaging (MRI) system for generating magnetic resonance images of a patient, comprising:
   a magnet subsystem including a magnet for generating a magnetic field, the magnet subsystem being located in a shielded room having a window;
   one or more physiological sensors located within the magnet, and adapted to receive data of the patient, the data associated with physiological parameters of the patient monitored by the sensor, at least one of the physiological sensors including a probe;
   an MRI control terminal for controlling the magnet subsystem, the MRI control terminal being located in a control room outside of the shielded room and comprising:
      a memory containing executable instructions; and
      a processor coupled to the memory and configured to use the executable instructions to:
         determine whether the data from the sensor meets a triggering condition;
         control the magnet subsystem such that the magnet subsystem initiates a pre programmed pulse sequence; and
   a data transmission subsystem for providing the data from the one or more physiological sensors to the MRI control terminal, comprising:
      a fiber optic cable directly coupled to the probe of the at least one of the physiological sensors;
      a wireless transmitter located outside of the magnet and in the shielded room, and coupled to the probe through the fiber optic cable; and
      a wireless receiver located in the control room and coupled to the MRI control terminal, the wireless receiver configured to wirelessly receive data transmitted by the wireless transmitter,
   wherein the wireless transmitter and wireless receiver are positioned with the window in between such that the data is wirelessly transmitted through the window, and
   wherein the MRI system is configured to:
      acquire a plurality of MRI data sets in response to determining that the data received wirelessly from the sensor meets the triggering condition, said data sets collected from radio frequency (RF) signals emitted from the patient as a result of the pre programmed pulse sequence; and
      generate a magnetic resonance image based on said data sets.

2. The MRI system of claim 1, wherein the MRI control terminal further includes a user interface for receiving the triggering condition from a user input.

3. The MRI system of claim 1, wherein the processor of the MRI control terminal is further configured to:
   identify the one or more sensors using an identifier signal that identifies at least one of the type of sensor, the sensor manufacturer, and a unique identifier; and
   select one of the identified sensors for receiving data from the sensor.

4. The MRI system of claim 1, wherein the processor of the MRI control terminal is further configured to:
   receive an input specifying a second triggering condition different from the first triggering condition;
   complete said acquisition for generating the MRI image using the second triggering condition.

5. The MRI system of claim 1, wherein the one or more physiological sensors include at least one of a photoplethysmograph, an oxymeter, and an EKG sensor.

6. The MRI system of claim 5, wherein the one or more physiological sensors include a photoplethysmograph, and wherein the triggering condition is one of a slope, amplitude, shape, pattern, frequency, and periodicity of a pressure pulse waveform of the patient.

7. The MRI system of claim 1, wherein the processor is configured to receive data representative of a waveform of one of a heartbeat, respiration, and a blood pulse of the patient.

8. The MRI system of claim 1, wherein the processor of the MRI control terminal is further configured to, after transmission of a first triggering signal, delay transmission of a second triggering signal.

9. The MRI system of claim 8, wherein the MRI control terminal further includes a user interface for receiving a user input indicating a duration of said delay.

10. The MRI system of claim 1, wherein the processor of the MRI control terminal is further configured to ignore the occurrence of a triggering condition based on the occurrence of a predetermined waveform pattern.

11. The MRI system of claim 1, wherein the processor of the MRI control terminal is configured to determine whether the data from the sensor meets a triggering condition that is indicative of a physiological event to be synchronized with said acquiring of the plurality of MRI data sets.

12. The MRI system of claim 1, wherein the fiber optic cable is plastic.

13. The MRI system of claim 1, wherein the data transmission subsystem further comprises an analog to digital converter adapted to receive an electric signal from at least one of the physiological sensors, filter and convert the electric signal, and provide the filtered and converted electric signal to the wireless transmitter, wherein the analog to digital converter is located outside of the magnet, and wherein the fiber optic cable extends into the magnet subsystem in order to connect the analog to digital converter to the probe.

14. The MRI system of claim 1, wherein the one or more physiological sensors includes a photoplethysmograph, the photoplethysmograph including a laser diode module and a photodiode module, wherein each of the laser diode module and photodiode module is connected to the probe through the fiber optic cable.

15. The MRI system of claim 14, wherein each of the laser diode module and photodiode module is located outside of the magnet.

\* \* \* \* \*